(12) United States Patent
Kovelman et al.

(10) Patent No.: US 6,326,480 B1
(45) Date of Patent: Dec. 4, 2001

(54) ANTISENSE REPORTER SYSTEM FOR ASSAYING RNA VIRUS REPLICATION

(75) Inventors: Robert Kovelman, La Jolla; Miguel Barbosa, San Diego, both of CA (US)

(73) Assignee: Signal Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 09/234,277

(22) Filed: Jan. 19, 1999

(51) Int. Cl.[7] .................................................. C07H 21/02
(52) U.S. Cl. .............................. 536/23.1; 935/27; 935/52
(58) Field of Search .......................... 536/23.1; 935/27, 935/52

(56) References Cited

U.S. PATENT DOCUMENTS

| 5,418,132 | 5/1995 | Olivo ........................................ 435/5 |
| 5,591,579 | 1/1997 | Olivo et al. ................................ 435/6 |

OTHER PUBLICATIONS

Olivo, "Transgenic Cell Lines for Detection of Animal Viruses," *Clinical Microbiology Reviews* 9(3): 321–334, 1996.

Olivo et al., "A Cell Line That Expresses a Reporter Gene in Response to Infection by Sindbis Virus: A Prototype for Detection of Positive Strand RNA Viruses," *Virology* 198: 381–384, 1994.

Park et al., "Rescue of a foreign gene by Sendai virus," *Proc. Natl. Acad. Sci. USA* 88: 5537–5541, 1991.

*Primary Examiner*—Hankyel T. Park

(57) ABSTRACT

Reporter systems for assaying positive sense RNA virus replication are provided. The reporter systems comprise a reporter gene in antisense orientation, flanked by the complements of 5' and 3' viral genome ends, such that exposure to an RNA-dependent RNA polymerase results in the generation of mRNA encoding an active reporter protein. Such systems may be used, for example, to detect active RNA virus and to monitor RNA virus therapies.

6 Claims, 1 Drawing Sheet

ANTISENSE REPORTER SYSTEM FOR ASSAYING RNA VIRUS REPLICATION

TECHNICAL FIELD

The present invention relates generally to the detection of RNA viruses. The invention is more particularly related to plasmid systems comprising an antisense reporter construct, which may be used to assay positive sense RNA virus replication.

BACKGROUND OF THE INVENTION

Many pathological conditions affecting humans and other animals are caused by infection with an RNA virus. Such viruses may be positive sense viruses (in which the viral genome has the same polarity as viral mRNA and may be directly translated), negative sense viruses (in which the viral genome is the complement of viral mRNA, and must be transcribed prior to translation) or double-stranded RNA viruses. Positive sense viruses include flaviviruses (e.g., hepatitis C virus); togaviruses (e.g., rubella virus, Sindbis virus, eastern and western encephalitis viruses) and picornaviruses (e.g., the enterovirus, polio virus, coxsackievirus, echovirus and rhinovirus).

In order to accurately diagnose and treat conditions caused by positive sense RNA virus infection, assays that are capable of sensitive detection of such viruses are needed. Most such assays focus on detecting the presence of viral nucleic acid and/or antigens. Such systems have the disadvantage that they cannot distinguish between active virus (capable of replication) and inactive virus, and they often lack the sensitivity that is necessary for a clinically reliable assay.

More recently, detection methods that take advantage of unique pathways of viral gene expression have been proposed. Such methods rely on the use of transgenic cell lines in which a virus-specific event triggers the production of a reporter protein. See Olivo, *Clinical Microbiology Reviews* 9:321–334, 1996; Park et al., *Proc. Natl. Acad. Sci. USA* 88:5537–5543, 1991; U.S. Pat. Nos. 5,591,579 and 5,418,132. However, it is unclear whether such systems can detect positive sense RNA viruses with the necessary sensitivity.

Accordingly, there is a need in the art for a system that permits the sensitive detection of active positive sense RNA viruses. The present invention fulfills this need and further provides other related advantages.

SUMMARY OF THE INVENTION

Briefly stated, the present invention provides antisense reporter systems for use in detecting active positive sense RNA viruses. Within certain aspects, the present invention provides antisense reporter plasmids, comprising a promoter operably linked to a DNA sequence encoding: (a) a sequence complementary to the 3' end of a viral genome; (b) a reporter gene in antisense orientation; and (c) a sequence complementary to the 5' end of the viral genome.

Within related aspects, the present invention provides antisense reporter mRNAs encoding: (a) a sequence complementary to a 3' end of a viral genome; (b) a reporter gene in antisense orientation; and (c) a sequence complementary to a 5' end of the viral genome.

Within certain embodiments of the above antisense reporter plasmids and antisense reporter mRNAs, the viral genome is a Hepatitis C virus genome. Reporter genes for use within such systems include, but are not limited to, chloramphenicol acetyl transferase, beta-galactosidase, alkaline phosphatase, green fluorescent protein, human growth factor and luciferase.

The present invention further provides, within other aspects, host cells transformed or transfected with an antisense reporter plasmid or antisense reporter mRNA as described above.

Within further aspects, the present invention provides methods for monitoring the level of RNA virus replication in an in vitro system, comprising the steps of: (a) contacting a cell as described above with a viral culture; and (b) determining a level of reporter gene expression in the cell, relative to a predetermined level in the absence of viral culture; and therefrom determining the level of RNA virus replication in an in vitro system.

Methods are also provided, within further aspects, for determining the effect of an agent on RNA virus replication in an in vitro system, comprising the steps of: (a) contacting a cell as described above with a viral culture and an agent; and (b) determining a level of reporter gene expression in the cell, relative to a predetermined level in the absence of agent; and therefrom determining the effect of an agent on RNA virus replication in an in vitro system.

Within further aspects, methods are provided for determining the presence or absence of an RNA virus in a sample, comprising the steps of: (a) contacting a cell as described above with a sample; and (b) determining a level of reporter gene expression in the cell, relative to a predetermined level in the absence of sample, and therefrom determining the presence or absence of an RNA virus in the sample. Suitable samples include biological samples isolated from a patient.

The present invention further provides, within other aspects, kits for determining the presence or absence of an RNA virus in a sample, comprising: (a) an antisense reporter plasmid as described above; and (b) a supply of reagents for detecting expression of the reporter gene.

Within further aspects, the present invention provides methods for monitoring the effectiveness of a therapy for RNA virus infection, comprising: (a) exposing a patient infected with an RNA virus to a candidate therapy; (b) contacting a sample obtained from the patient with a cell transformed or transfected as described above; and (c) determining a level of expression of the reporter gene, relative to a predetermined level for cells contacted with a second sample obtained from the patient, wherein the second sample was obtained prior to the candidate therapy, and therefrom monitoring the effectiveness of the candidate therapy.

Within further aspects, methods are provided for detecting a drug resistant RNA virus, comprising: (a) exposing a sample obtained from a patient infected with an RNA virus to a drug; (b) contacting the sample with a cell as described above; and (c) determining a level of expression of the reporter gene, relative to a predetermined level for cells contacted with a second sample obtained from the patient, wherein the second sample is not exposed to the drug, and therefrom identifying a drug resistant RNA virus.

These and other aspects of the present invention will become apparent upon reference to the following detailed description and attached drawings. All references disclosed herein are hereby incorporated by reference in their entirety as if each was incorporated individually.

Figure 1:
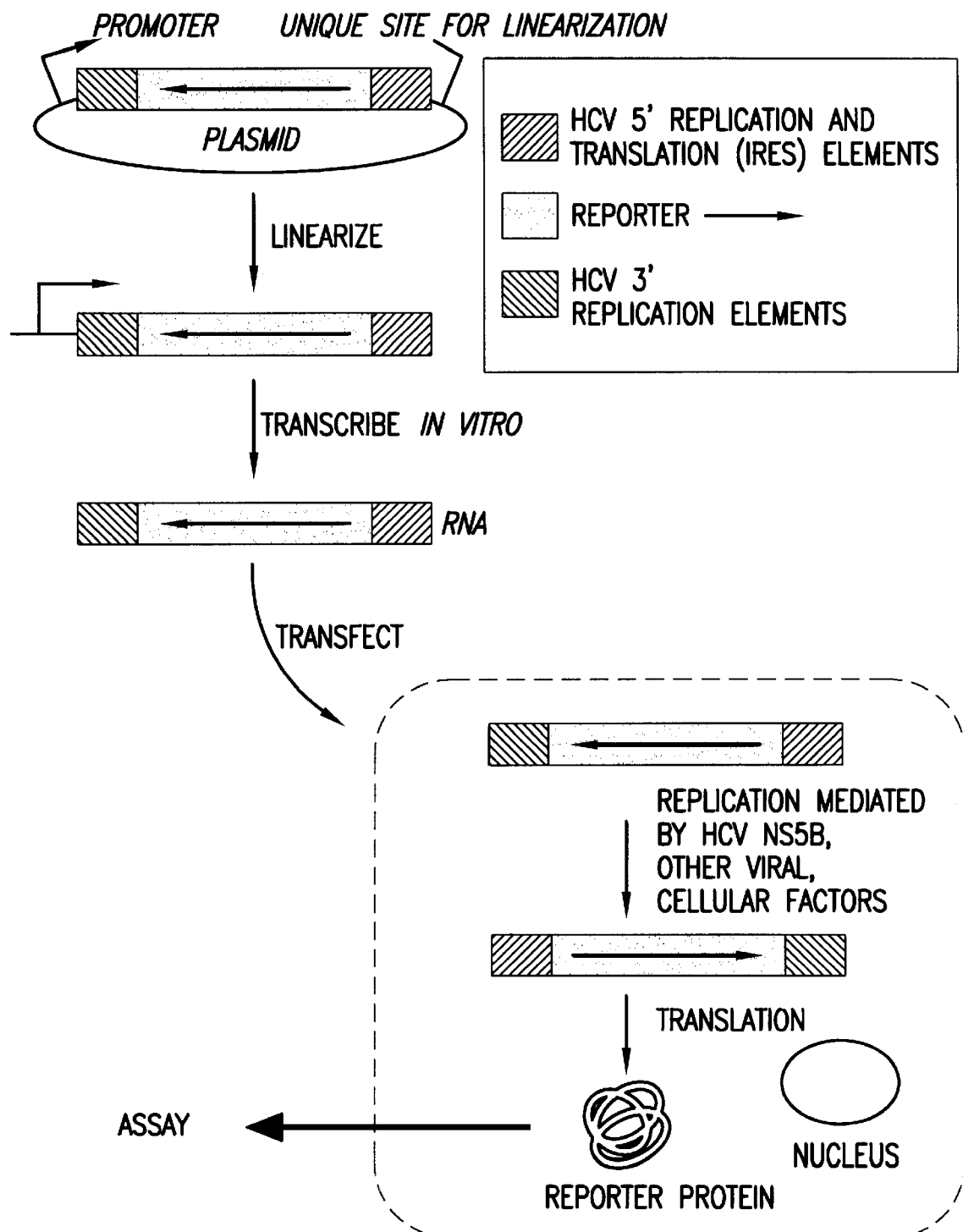
FIG. 1 is a diagram illustrating the use of a representative antisense reporter plasmid system. A reporter in antisense orientation is inserted between hepatitis C virus genome ends, such that a transcript will contain the complement of the 3' end of the viral genome, the reporter in antisense orientation and the complement of the 5' end of the viral genome. The plasmid is linearized and transcribed in vitro. The resulting mRNA is transfected into a host cell. In the presence of viral and cellular factors necessary for viral replication and translation, active reporter protein is generated and detected using a suitable assay.

DETAILED DESCRIPTION OF THE INVENTION

As noted above, the present invention is generally directed to systems comprising antisense reporters for use in detecting the presence of active positive sense RNA virus. Such plasmids support the transcription of mRNA encoding viral genome end complements flanking an antisense reporter sequence. In the presence of active viral RNA-dependent RNA polymerase, the transcript is replicated into an RNA molecule that can be translated into active reporter protein. Such systems may be used, for example, to detect active RNA virus, as well as to study endogenous factors involved in viral replication and to screen agents for the ability to modulate viral replication. Agents identified using antisense reporter systems provided herein may be used, for example, for the treatment or prevention of viral infections.

An "antisense reporter plasmid," as used herein, is a DNA plasmid that supports the synthesis of a transcript comprising, in order, (a) a complement of a 3' viral genome end; (b) the complement of a reporter gene (i.e., the reporter in antisense orientation) and (c) a complement of a 5' viral genome end. In other words, such a plasmid comprises a promoter operably linked to a sequence that encodes the viral genome end complements and antisense reporter gene. Viral genome ends may be derived from any positive sense RNA virus (e.g, Hepatitis C virus, poliovirus, rhinovirus or hepatitis G virus), and may be readily identified and cloned by those of ordinary skill in the art. An antisense reporter plasmid should further comprise an origin of replication that permits replication in a desired host cell. Optionally, an antisense reporter plasmid may comprise any of a variety of additional components, such as a selectable marker.

Any reporter gene known in the art may be used within such plasmids, provided that expression can be readily monitored. Expression of a reporter gene may be determined at the transcriptional level (i.e., using any of a variety of well known hybridization or amplification techniques to assess the level of mRNA transcribed from the reporter gene), at the translational level (i.e., using a compound, such as an antibody, that binds to the protein encoded by the reporter gene to assess the level of such protein synthesized in any standard assay format, such as ELISA) or at the level of activity (i.e., using an assay to measure an activity (e.g., enzymatic) of a protein encoded by the reporter gene). Preferably, reporter gene expression is determined by measuring an activity of the encoded protein. Suitable reporter genes include, but are not limited to, luciferase (e.g., firefly or Renilla), green fluorescent protein, β-galactosidase and chloramphenicol acetyl transferase, alkaline phosphatase and human growth factor. Antisense reporter plasmids may be maintained in suitable host cells, which may be transformed or transfected using well known techniques.

For use in detecting RNA virus in a sample, antisense reporter plasmids are generally linearized and transcribed in vitro, to generate antisense reporter mRNA. This reporter mRNA is then transfected into a suitable host cell. In general, any cell that expresses or can be supplemented with factors necessary for viral infection may be used as a host cell. Suitable host cells include, but are not limited to, HeLa cells and primary culture cells. Host cells may be transformed or transfected with an antisense reporter mRNA using standard techniques known in the art to be appropriate for the particular cell type. Transformed or transfected host cells are specifically contemplated by the present invention.

The antisense reporter systems provided herein may be used to determine the presence or absence of an RNA virus in a sample. Samples that may be assayed include, but are not limited to, biological samples obtained from a warm-blooded animal, such as a human patient. Human biological samples may be, for example, urine, throat secretions, genital secretions, breast milk, blood or a fraction of any of the foregoing samples. A fluid sample may also be prepared from a solid material by extraction or other procedures common in the art. It will be evident to those of ordinary skill in the art that one or more preparatory steps, such as centrifugation, may be desirable to place a sample in optimal condition for testing.

To determine whether a sample contains a particular RNA virus, the sample is contacted with a host cell transformed or transfected as described above for a suitable amount of time, and the effect of the sample on reporter expression may be evaluated by measuring the level and/or activity of the reporter mRNA or protein. Standard techniques may be employed, such as PCR or hybridization (for evaluating levels of mRNA) or any of a variety of immunoassays or functional assays appropriate for the reporter protein employed. In many cases, a reporter protein is an enzyme capable of detection by routine colorimetric, fluorometric or luminometric techniques, and assays appropriate for particular reporter genes are well known in the art. For example, luciferase activity may be detected using standard luminometric methods, with luciferin as the enzyme substrate (de-Wet et al., *Mol. Cell. Biol.* 7:725–737, 1987). Commercially available luciferase assays are available from, for example, Promega (Madison, Wis.). Appropriate methods for detecting the level of expression of other reporter genes will be apparent to those of ordinary skill in the art and may be found, for example, in Sambrook et al., *Molecular Cloning: A Laboratory Manual*, Cold Spring Harbor Laboratories, Cold Spring Harbor, N.Y., 1989 and in manufacturer protocols.

In general, a signal detected in a reporter protein assay is compared to a signal that corresponds to a predetermined cut-off value. This cut-off value is preferably the average mean signal obtained from cells incubated in the absence of RNA virus. In general, a sample generating a signal that is at least two-fold above the mean is considered positive is considered positive for RNA virus. The above assay may also be used to determine the amount of RNA virus in a sample. Absolute levels of RNA virus may be obtained by comparing the signal generated by a sample with the signal generated by standards having known amounts of the virus, using techniques well known to those of ordinary skill in the art. As discussed in more detail below, the determination of relative levels of RNA virus may also be useful in, for example, monitoring a therapy for RNA virus infection or evaluating the response of a RNA virus isolate to a given drug (e.g., in identifying drug resistance).

The antisense reporter systems provided herein may be used to monitor the level of RNA virus replication in an in vitro system. Within such methods, a culture comprising an RNA virus is contacted with a host cell transformed or transfected as described above for a suitable amount of time, and the level of reporter expression may be evaluated as described above. This level is generally determined relative to a predetermined level in the absence of viral culture. This assay can be used for quantitative determination of RNA virus replication or to monitor the changes in the ability of an RNA virus to replicate over time.

Similarly, an antisense reporter system may be used to determine the effect of an agent on RNA virus replication in an in vitro system. Within such methods, a culture comprising an RNA virus is contacted with an agent prior to or during contact with a host cell transformed or transfected as described above for a suitable amount of time. The level of reporter expression may be evaluated as described above, relative to the level observed in the absence of agent. The agent may be any compound whose effect on RNA virus replication is to be determined. Assays for RNA virus replication may be used as primary screens (e.g., to screen a cDNA expression library or a small molecule combinatorial library) or as secondary screens (i.e., to characterize a particular agent previously identified as a possible antiviral agent).

Detection of RNA virus by the method described above may also be useful for identifying drug-resistant RNA viruses and for monitoring therapy. In these aspects, the change in the level of RNA virus in response to exposure to a drug or other therapy is evaluated. To evaluate whether an RNA virus is resistant to a given drug, a sample containing the virus is exposed to a suitable amount of the drug, using methods appropriate for the sample type which will be apparent to those of ordinary skill in the art. Following exposure, the sample is then tested for the presence of RNA virus as described above. If the RNA virus in the treated sample is resistant to the particular drug, RNA virus will be detected. It should be noted that the level of drug resistant RNA virus that is detected in the sample may temporarily decrease in response to treatment. Nonetheless, the RNA virus is considered drug resistant if either the signal is unchanged after 2–4 weeks of treatment, or if the signal initially decreases after 2–3 weeks of treatment and thereafter increases at a follow-up evaluation.

To evaluate the effectiveness of a therapy for RNA virus infection, suitable samples obtained from one or more infected patients are first evaluated for RNA virus as described above. The candidate therapy is then applied to the patient(s) and the level of RNA virus following treatment is determined. For example, blood drawn from an infected patient may be tested for the presence of RNA virus prior to treatment. After 2–4 weeks of treatment, a second blood sample may be drawn and tested for the RNA virus. A therapy is considered effective if the therapy lowers the level of RNA virus by at least two-fold. Once a therapy is found to be effective, further treatment of patients may be monitored by performing similar RNA virus assays at intervals of about 2–4 weeks until RNA virus is no longer detectable.

Antisense reporter systems as described herein have the advantage over other assays, in that only samples containing active virus (i.e., virus having an active RNA-dependent RNA polymerase) are detected. This results in a sensitive assay for infectious RNA virus. This assay further is suitable for high-throuput screening formats. As schematic diagram illustrating a the use of an antisense reporter plasmid system as described herein is provided in FIG. 1.

The present invention further provides kits for use in detecting the presence of RNA virus in a sample. Such kits typically comprise two or more components necessary for performing such an assay. Such components may be compounds, reagents and/or containers or equipment. For example, one container within a kit may contain a host cell line suitable for transfection with an antisense reporter mRNA construct. Alternatively, or in addition, a kit may provide an antisense reporter plasmid, or antisense reporter mRNA, for use within an assay. One or more additional containers may enclose elements, such as reagents or buffers, to be used in an assay to detect expression of a reporter gene or the level of plasmid replication.

The following Examples are offered by way of illustration and not by way of limitation.

EXAMPLES

Example 1
Preparation of Antisense Reporter Plasmid

This Example illustrates the preparation of an antisense reporter plasmid system suitable for detecting Hepatitis C virus.

Oligonucleotide primers are designed to amplify in separate reactions via PCR the coding region for the firefly luciferase protein, the 5' untranslated region (5' UTR) of HCV, and the 3' untranslated region (3' UTR) of HCV. In addition to the sequences required for hybridization and subsequent amplification of these fragments, the oligonucleotides are also designed with nonhomologous sequences at their 5' ends such that following amplification, digestions by restriction enzymes are performed and ligation of the digested fragments results in the creation of a fragment containing sequences in the order 5' UTR-luciferase-3' UTR. A second PCR reaction is performed to amplify this entire fragment, followed by restriction enzyme digestion to produce ends compatible for cloning into a plasmid vector containing the T7 RNA polymerase promoter (pBluescript SK, available from Stratagene) in an orientation such that the 3' UTR is closest to the site of transcription initiation. Subsequent improvement of this construct can be performed by site-directed mutagenesis to eliminate the restriction sites introduced between the regions, between the T7 promoter and the 3' UTR, and downstream of the 5' UTR.

Example 2
Detection of Hepatitis C Virus

This Example illustrates the use of an antisense reporter plasmid system for the detection of Hepatitis C virus.

A plasmid as described in Example 1 is digested by a restriction enzyme for which there is a cleavage site immediately downstream of the 5' UTR in the reporter plasmid. Following purification of the digested DNA, transcription by T7 RNA polymerase is performed. After the reaction is stopped, DNase is used to digest the DNA template, and the RNA is purified. The RNA is transfected via a lipid-based method into cells which express proteins supporting replication of the parent virus. Cells are lysed after a suitable period of time (12–48 hours), and luciferase activity is determined by standard methods. Only cells that can replicate the RNA molecule and translate the resultant RNA complement give a positive luciferase signal.

From the foregoing, it will be appreciated that, although specific embodiments of the invention have been described herein for the purpose of illustration, various modifications may be made without deviating from the spirit and scope of the invention. Accordingly, the present invention is not limited except by the appended claims.

What is claimed is:

1. An antisense reporter plasmid, comprising a promoter operably linked to a DNA sequence encoding:
   (a) a sequence complementary to the 3' end of a viral genome;
   (b) a reporter gene in antisense orientation; and
   (c) a sequence complementary to the 5' end of the viral genome.

2. An antisense reporter plasmid according to claim 1, wherein the viral genome is a Hepatitis C virus genome.

3. An antisense reporter plasmid according to claim 1, wherein the reporter gene encodes a protein selected from the group consisting of chloramphenicol acetyl transferase, beta-galactosidase, alkaline phosphatase, green fluorescent protein and human growth factor.

4. An antisense reporter plasmid according to claim 1, wherein the reporter gene encodes a luciferase.

5. A host cell transformed or transfected with an antisense reporter plasmid according to claim 1.

6. A cell according to claim 5, wherein the cell is present within a primary cell culture.

* * * * *